US00PP37053P2

(12) United States Plant Patent
Hansen

(10) Patent No.: US PP37,053 P2
(45) Date of Patent: Oct. 21, 2025

(54) ***HOSTA* PLANT NAMED 'Awakening Spirit'**

(50) Latin Name: ***Hosta* hybrid (Tratt.)**
Varietal Denomination: Awakening Spirit

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 18/831,380

(22) Filed: Dec. 20, 2024

(51) Int. Cl.
*A01H 5/12* (2018.01)
*A01H 6/12* (2018.01)

(52) U.S. Cl.
USPC ..... Plt./353
CPC ..... *A01H 6/12* (2018.05)

(58) Field of Classification Search
USPC ..... Plt./353
See application file for complete search history.

*Primary Examiner* — Susan Mccormick Ewoldt

(57) ABSTRACT

A new and distinct *Hosta* plant named 'Awakening Spirit' producing large-sized rounded mounds of basal, broadly-cordate to rounded, large-sized leaves with acute apices, cordate bases, and slightly wavy margins. The leaves are variegated having glaucous bluish-green margins and centers that begin the season chartreuse and become creamy as the season progresses with intermediate colors between the margin and center of variably large segments of several shades of chartreuse. The campanulate flowers are near pale purple just above the foliage beginning in late June. 'Awakening Spirit' is useful in the landscape, as a container plant, a specimen or en masse.

3 Drawing Sheets

Botanical classification: *Hosta* hybrid (Tratt.).
Variety denomination: 'Awakening Spirit'.

STATEMENT REGARDING PRIOR DISCLOSURES UNDER 37 CFR 1.77(B)(6)

*Hosta* 'Awakening Spirit' was first introduced by the inventor as a non-enabling description in registration of the name in early 2024 with the International Cultivar Registration Authority for the genus *Hosta*. No plants of *Hosta* 'Awakening Spirit' have been sold or offered for sale in this country or anywhere in the world, nor has any enabling disclosure of the new plant been made.

BACKGROUND AND ORIGIN OF THE PLANT

The present invention relates to a new and distinct *Hosta* plant, *Hosta* 'Awakening Spirit' hereinafter also referred to as the new plant or by the cultivar name 'Awakening Spirit'. *Hosta* 'Awakening Spirit' was hybridized by the inventor on Jun. 23, 2014, at a wholesale perennial nursery in Zeeland, Michigan, USA. The female parent was the proprietary unreleased seedling known only by the code WGI-33 (not patented) and the male parent was the proprietary unreleased seedling known only by the code 11-55-3 (not patented). The seeds from this cross were collected and planted in the fall of 2014 and a single seedling from this cross eventually was selected as the new plant. The new plant was assigned the breeder code 14-91-1 and passed the initial evaluation in the summer of 2016.

'Awakening Spirit' has been asexually propagated by division at the same nursery since 2018 and also by careful shoot tip plant tissue culture with the resultant asexually propagated plants having retained all the same traits as the original plant. *Hosta* 'Awakening Spirit' has been stable and reproduced true to type plants in successive generations of asexual reproduction.

There are over 7,000 registered and established *Hosta* cultivars with The American *Hosta* Society, which is the International Cultivar Registration Authority for the genus *Hosta*. Several of these are variegated with blue-green leave margins and blades. The most similar *Hosta* cultivars known to the applicant are: 'Alligator Alley' (not patented), 'Avant Garde' U.S. Plant patent application Ser. No. 18/831,373, 'Lakeside Beach Captain' (not patented), 'Lakeside Shoremaster' (not patented), 'Queen of Islip' (not patented), 'Sound of Music' U.S. Plant Pat. No. 35,563, and 'When I Dream' U.S. Plant Pat. No. 34,285.

'Alligator Alley' has foliage that is more bullate, more cupped and the margin is less sinuate. 'Avant Garde' has a taller and more upright habit with larger foliage that is less bullate. 'Lakeside Beach Captain' has a smaller habit, smaller leaves, and the variegated margin is wider in proportion and the center is narrower and the edge is flatter and less sinuate. 'Lakeside Shoremaster' is smaller in habit and has smaller foliage that is narrower and more ovate and the edge is flatter and less sinuate. 'Sound of Music' has a larger habit, larger foliage that is more ovate and less rounded. 'When I Dream' is longer, less rounded foliage with more acute apex, the margin is more sinuate the habit is smaller, and the flowers are lighter pale lavender on shorter scapes.

The female parent is larger in habit, with larger, more bullate, more upwardly facing, that is randomly streaked with creamy yellow variegation, and the scapes are shorter. The male parent has a more horizontal habit with solid bluish-green foliage that is more wedge-shaped.

Other *Hosta* cultivars may have some individual traits similar to 'Awakening Spirit', but the new plant differs from the above-listed cultivars and all other *Hostas* known to the applicant by the combination of the following traits.

1. Leaves are large, broadly-cordate to rounded, with acute apices and cordate bases;
2. Leaves have a slightly wavy margin, moderately bullate surface between the veins, and deeply impressed adaxial veins, with a tendency for the leaf ends to cup downward;
3. Leaf margins are moderately glaucous bluish-green, and the center color emerges chartreuse becoming creamy as the season progresses;
4. Leaves have a series of intermediate colors of several shades of chartreuse between the margin and center of variably large segments;
5. Campanulate flowers are pale purple on upright scapes beginning in late June;
6. Flowers are subtended by a small lightly-blushed bract of similar color to foliage and flowers and densely arranged on scapes with the first flowers beginning to open just above the foliage;
7. The habit is a large-sized rounded mound.

BRIEF DESCRIPTION OF THE DRAWINGS

The photographs of the new plant demonstrate the overall appearance of the new plant, including the unique traits. The colors are as accurate as reasonably possible with color reproductions. Ambient light spectrum, temperature, source and direction may cause the appearance of minor variation in color.

The drawings show a nine-year-old plant of 'Awakening Spirit' in a trial garden at a nursery in Zeeland, MI with supplement fertilizer and water as needed.

DETAILED BOTANICAL DESCRIPTION

Figure 1:
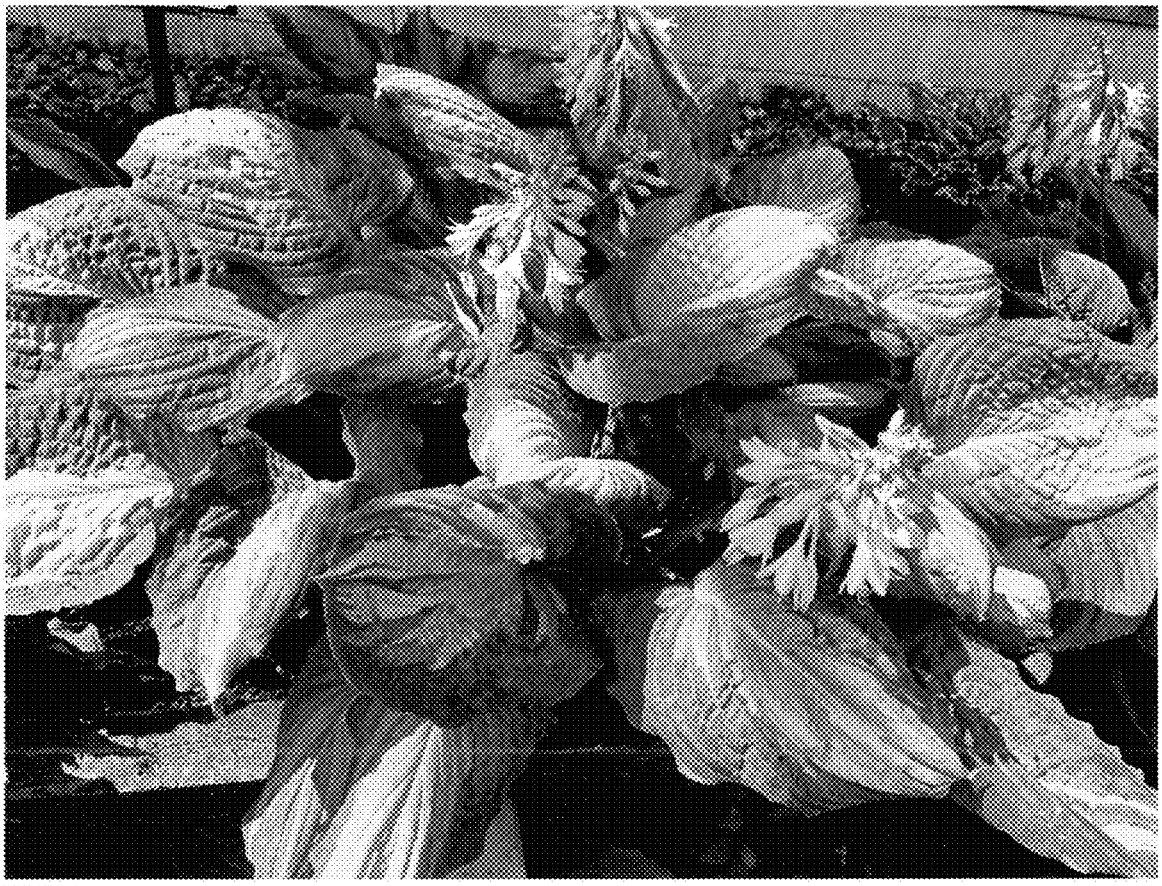
FIG. 1 shows the landscape habit of a plant at early flowering.
Figure 2:
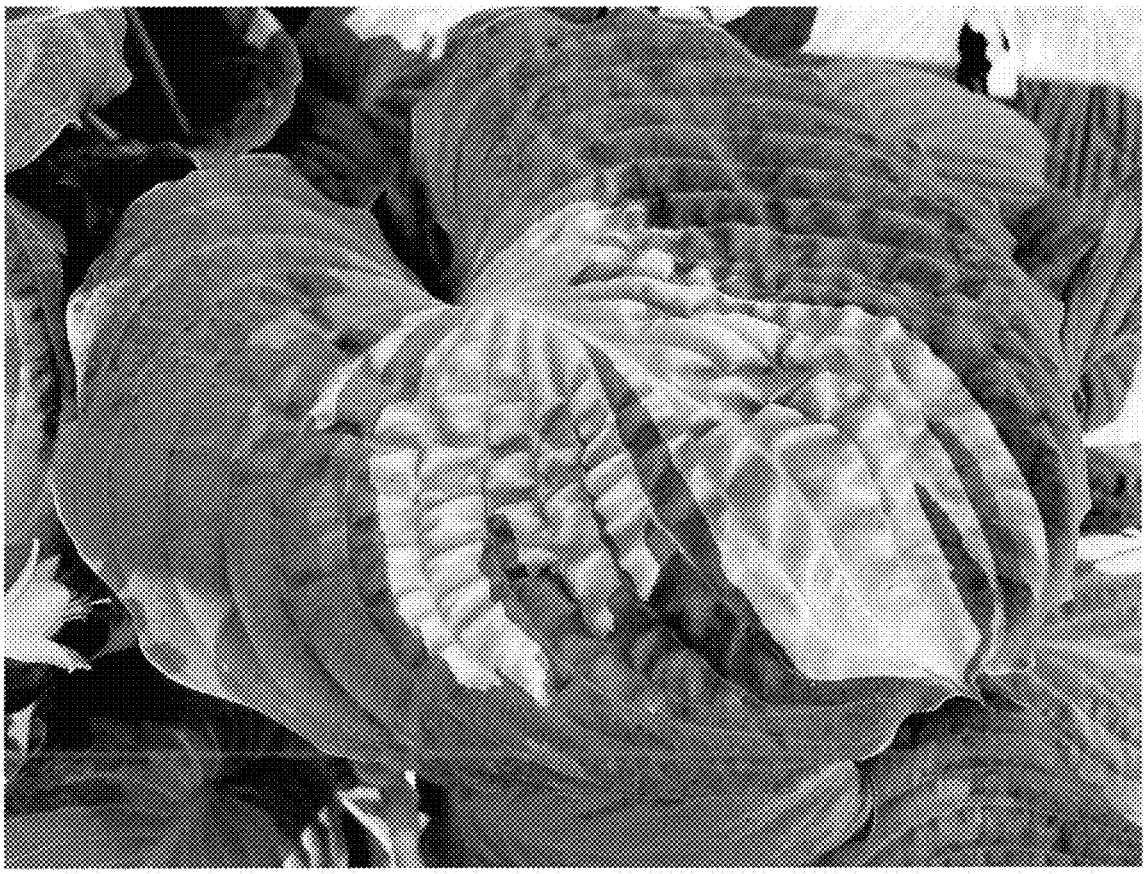
FIG. 2 shows a close-up of a leaf at flowering.
Figure 3:
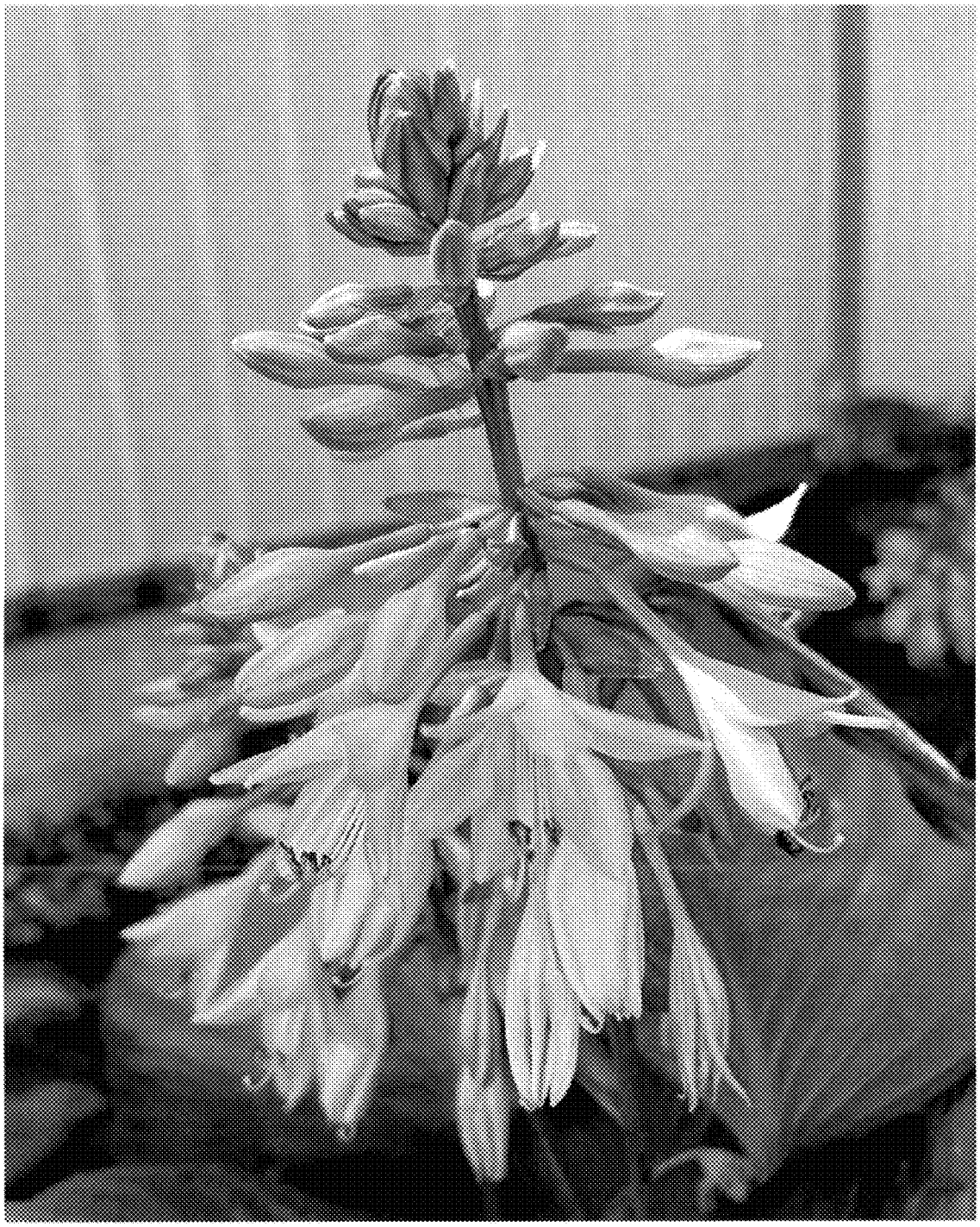
FIG. 3 shows a close-up of the flowers, buds, and foliar bracts of a plant.

The following descriptions and color references are based on the 2015 edition of The Royal Horticultural Society Colour Chart except where common dictionary terms are used. The new plant, *Hosta* 'Awakening Spirit', has not been observed under all possible environments. Those skilled in the art will appreciate that certain characteristics will vary with plants that are more mature or plants that are less mature. The phenotype may vary slightly with different environmental conditions, such as temperature, light, fertility, moisture and maturity levels, but without any change in the genotype. The following observations and size descriptions are of a five-year-old plant in a shaded trial garden in Zeeland, Michigan with supplemental water and fertilizer.

Botanical classification: *Hosta* x hybrid;

Parentage: Female or seed parent is a proprietary hybrid known only as WGI-33; male or pollen parent is 11-55-3;

Propagation: Garden division and sterile shoot tip tissue culture;

Time to initiate roots from tissue culture: About three to four weeks;

Growth rate: Moderately vigorous to slow;

Crop time: About four months to six months to finish during the spring in a one-liter container from rooted tissue culture plantlet during the warm portion of the growing season;

Rooting habit: Fleshy, lightly branching;

Root color: Nearest RHS NN155C when actively growing;

Plant shape and habit: Hardy herbaceous perennial with basal rosette of leaves emerging from rhizomes producing a very large-sized mound of outwardly arching petioles and leaves and mostly erect scapes flowering just above the foliage;

Plant size: Foliage height to about 71 cm above soil line to the top of the leaves, to about 86 cm tall to the top of the flowers, and to about 140 cm wide at the widest point about 20 cm above the soil line;

Foliage description: Broadly-cordate to rounded; broadly acute apex; cordate base with lobes nearly overlapping; margin entire, and weakly sinuate; not folded, with distal portion frequently curved downward producing an inverted cupped form; surface moderately bullate between the veins; glabrous and moderately glaucous both surfaces; flexible; variegated;

Leaf blade size: To about 28 cm long and about 26 cm wide about halfway from the petiole;

Leaf blade color: Early season and expanding adaxial margin nearest RHS 137A, center between RHS 146D and RHS N144A, with intermediate zone comprising between RHS 146D and RHS 144A, abaxial margin between RHS N138C and RHS 138A, center RHS 146D; mid-season and mature adaxial margin between RHS 137A and RHS NN137B, center nearest RHS 11C, with intermediate zone comprising colors of between RHS 193B and RHS 160D, between RHS 193A and RHS 148D, between RHS 144A and RHS N144A, abaxial margin between RHS 190A and RHS N138D, center nearest RHS 11D, with intermediate zone comprising colors of between RHS 194C and RHS 147D, between RHS 147C and RHS 146D, and between RHS 138B and RHS 194B;

Veins: 14 to 16 pairs with midrib; moderately impressed adaxial and costate and smooth abaxial;

Vein color: Adaxial mature margin region nearest RHS 147C and center region nearest RHS 158B, abaxial margin nearest RHS 148C, center nearest RHS 158C; emerging adaxial margin nearest RHS 146D, center nearest RHS 146D; emerging abaxial margin between RHS 193A and RHS 148D, center nearest RHS 193A;

Petiole: Glabrous and matte both adaxial and abaxial; moderately concavo-convex; stiff; to 41.5 cm long and 20 mm wide at base and about 5 mm deep at base;

Petiole color: Adaxial margin nearest RHS 137C, center between RHS 145A and RHS 146D, abaxial margin nearest RHS N138B, midrib between RHS 139D and RHS 145D, and region surrounding midrib between RHS 145B and RHS 146D;

Flower description:

Inflorescence: With about 44 flowers in the upper flowering portion; about 28 cm long and 7 cm wide; with single bract subtending each flower; flowering in the upper 28 cm of peduncle, and to about 12 cm across;

Buds one to two days prior to opening: Clavate with acute apex and narrow tube and rounded base; about 49 mm long and 13 mm in diameter at the widest portion in the bulb, tube to about 22 mm long and to about 4 mm diameter at base, tapering below bulb;

Bud color: Bulb portion between RHS 76D and RHS 84D, tube portion between RHS 76D and RHS 76C;

Flowers: Perfect; incomplete; campanulate flaring distally; attitude slightly downwardly; to 58 mm long to exserted pistil; corolla to 55 mm long and 34 mm wide at apex, corolla tube portion 23 mm long, and about 3.5 mm diameter in the middle; with rounded base; decreasing in size distally; flowers tightly arranged on distal portion of scape; aspect mostly horizontal;

Flowering lasting: Persists for a normal period, usually about one day on plant;

Flowering period: Scapes remain effective with flowers beginning late June for about three to three and a half weeks; with about 44 flowers per scape; mostly secund;

Fragrance: No detectable fragrance;

Tepal: Two sets of three, nearly identical; clavate; entire margins; acute apex; fused in basal 31 mm; glabrous adaxial and abaxial; outer set to about 11 mm wide and 55 mm long; inner set to about 55 mm long and 12 mm wide; without a translucent margin;

Tepal color: Outer and inner sets adaxial center between RHS 76C and RHS 76B continuing through tube to base, and margin nearest NN155D; outer and inner sets abaxial flared portion between RHS 76D and RHS 85D, tube portion nearest RHS 84D with basal 2 mm nearest RHS 85C;

Gynoecium: Single; to about 59 mm long; superior;

*Style*.—Cylindrical; glabrous; to about 52 mm long and 0.7 mm diameter; proximally straight with distal 10 mm arcuate upwards about 90°; color nearest RHS 155C.

*Stigma*.—Puberulent; globose; about 1 mm long and 2 mm diameter; color nearest RHS NN155A.

*Ovary*.—Oblong ellipsoidal; superior; apex rounded; base rounded to truncate; sides moderately fluted longitudinally; about 6 mm long and 3 mm diameter; color between RHS 145C and RHS 145B.

Androecium: Six;

*Filaments*.—Six; cylindrical; approximately 55 mm long and 0.5 mm in diameter; arcuate upwardly about 90° in the distal 10 mm; color nearest RHS NN155B.

*Anthers*.—Oblong with rounded ends; dorsifixed, longitudinally dehiscent; about 4 mm long and 2 mm wide when fully developed; color nearest RHS N186C.

*Pollen*.—Abundant; spherical; minute; color between RHS 17A and RHS 15A.

Peduncle: Cylindrical; usually one per mature division; about 3 per plant; glabrous; moderately glaucous; aspect upwardly; to about 86 cm tall, and about 10 mm in diameter at base; Peduncle color: between RHS 138A and RHS 137C;

Pedicel: Cylindrical; glabrous; slightly lustrous; curved slightly downward; to about 11 mm long and 2 mm diameter, decreasing distally;

Pedicel color: Distally nearest RHS NN155C and the proximal 1 to 2 mm nearest RHS 146D;

Floral bracts: Each flower normally subtended by a single bract; lanceolate; narrowly acute apex and truncate clasping base; entire margin; strongly concavo-convex; glabrous and slightly glaucous abaxial and adaxial; to about 35 mm long 16 mm wide, decreasing distally;

Bract color: Bracts at time of flowering adaxial and abaxial proximal center nearest RHS 155C and distal center variable nearest RHS N148D, between RHS N148D and RHS 146D, and variably blushed with nearest RHS N77D, margins nearest RHS 147B;

Fruit: Non-fleshy, dehiscent, tri-loculicidal capsule; oblong; rounded base; acute to apiculate apex; about 33 mm long and 7 mm in diameter; color as maturing nearest RHS 138B, upon maturity nearest RHS 161C;

Seeds: Elliptic; with flattened wing surrounding embryo positioned toward one end of ellipse; to about 10 mm long, 3 mm wide and 1 mm thick at embryo; typically, 18 to 36 per capsule; color between RHS 200A and RHS 202A with maturity;

Disease and pest resistance: The thick glaucous leaves provide some resistance to slug feeding. Other resistance to pests (including: *Odocoileus virginianus* and *Oryctotagus cuniculus*) and diseases common to *Hostas* is equal that typical of other cultivars.

Growth: The plant grows best and shows its best coloration with plenty of moisture, adequate drainage and light shade, but the plant is able to tolerate some drought when mature.

Hardiness: At least from USDA zone 3 through 8.

It is claimed:

1. A new and distinct *Hosta* plant named 'Awakening Spirit' as herein described and illustrated.

* * * * *